United States Patent [19]
East

[11] Patent Number: 4,867,740
[45] Date of Patent: Sep. 19, 1989

[54] MULTIPLE-MEMBRANE FLOW CONTROL VALVE AND IMPLANTABLE SHUNT SYSTEM

[75] Inventor: Gary P. East, Santa Barbara, Calif.

[73] Assignee: Pudenz-Schulte Medical Research Corp., Goleta, Calif.

[21] Appl. No.: 173,092

[22] Filed: Mar. 24, 1988

[51] Int. Cl.$^4$ .............................................. A61M 27/00
[52] U.S. Cl. ...................................... 604/9; 604/247; 137/854
[58] Field of Search ...................................... 604/8–10, 604/247; 137/512, 854; 417/566

[56] References Cited

U.S. PATENT DOCUMENTS

| | | |
|---|---|---|
| 2,969,066 | 1/1961 | Holter et al. |
| 3,020,913 | 2/1962 | Heyer |
| 3,233,610 | 2/1966 | Wade |
| 3,288,142 | 11/1966 | Hakim |
| 3,452,757 | 7/1969 | Ames |
| 3,527,226 | 9/1970 | Hakim |
| 3,566,875 | 3/1971 | Stoehr |
| 3,595,240 | 7/1971 | Mishler |
| 3,654,932 | 4/1972 | Newkirk et al. |
| 3,674,050 | 7/1972 | Kuffer et al. |
| 3,683,929 | 8/1972 | Holter |
| 3,690,323 | 9/1972 | Wortman et al. |
| 3,758,073 | 9/1973 | Schulte |
| 3,769,982 | 11/1973 | Schulte |
| 3,827,439 | 8/1974 | Schulte et al. |
| 3,886,948 | 6/1975 | Hakim |
| 3,889,687 | 6/1975 | Harris et al. |
| 3,924,635 | 12/1975 | Hakim |
| 3,985,140 | 10/1976 | Harris |
| 3,991,768 | 11/1976 | Portnoy |
| 3,999,553 | 12/1976 | Spitz et al. |
| 4,156,422 | 5/1979 | Hildebrandt et al. |
| 4,190,040 | 2/1980 | Schulte |
| 4,215,695 | 8/1980 | Spitz et al. |
| 4,332,255 | 6/1982 | Hakim et al. |
| 4,387,715 | 6/1983 | Hakim et al. |
| 4,443,214 | 4/1984 | Marion |
| 4,464,168 | 8/1984 | Redmond et al. |
| 4,540,400 | 9/1985 | Hooven |
| 4,551,128 | 11/1985 | Hakim et al. |
| 4,552,553 | 11/1985 | Schulte et al. |
| 4,557,721 | 12/1985 | Hooven |
| 4,560,375 | 12/1985 | Schulte et al. |
| 4,578,057 | 3/1986 | Sussman |
| 4,583,967 | 4/1986 | Harris |
| 4,588,394 | 5/1986 | Schulte et al. |
| 4,595,390 | 6/1986 | Kakim et al. |
| 4,601,724 | 7/1986 | Hooven et al. |
| 4,605,395 | 8/1986 | Rose et al. |
| 4,627,832 | 12/1986 | Hooven et al. |
| 4,631,051 | 12/1986 | Harris |
| 4,636,194 | 1/1987 | Schulte et al. |
| 4,673,384 | 6/1987 | Marion |
| 4,675,003 | 6/1987 | Hooven |
| 4,676,772 | 6/1987 | Hooven |
| 4,681,559 | 7/1987 | Hooven |
| 4,735,607 | 4/1988 | Keith, Jr. ........................... 137/854 |

FOREIGN PATENT DOCUMENTS 2444452 5/1975 Fed. Rep. of Germany .
1135947 1/1985 U.S.S.R. .

OTHER PUBLICATIONS

The Lancet, vol. 1.(64) 7326, p. 202; Jan. 25, 1964.
Surgical Forum, #2, 1951, by Frank E. Nulsen, M.D. and Eugene B. Spitz, M.D., pp. 399–402.

Primary Examiner—Stephen C. Pellegrino
Attorney, Agent, or Firm—Kelly, Bauersfeld & Lowry

[57] ABSTRACT

A surgically implantable shunt system, including a flow control valve and an antechamber, is provided for controlling the release of entrapped body fluids. The flow control valve includes a pair of molded plastic bases situated, respectively, adjacent to an inlet and an outlet of the valve, which bases are situated within a flexible encasement. Each base includes an outer housing, a valve membrane carrier positioned within the housing, and a flow control member. The flow control members each include a central support and a resilient membrane which is generally arch-shaped and resiliently biased to contact the respective base generally along the outer edge of the membrane in a manner permitting only controlled one-way flow through the valve. The antechamber permits injection of medication into the shunt between a proximal catheter and the distally located flow control valve, and pumping of the medication in either direction.

18 Claims, 2 Drawing Sheets

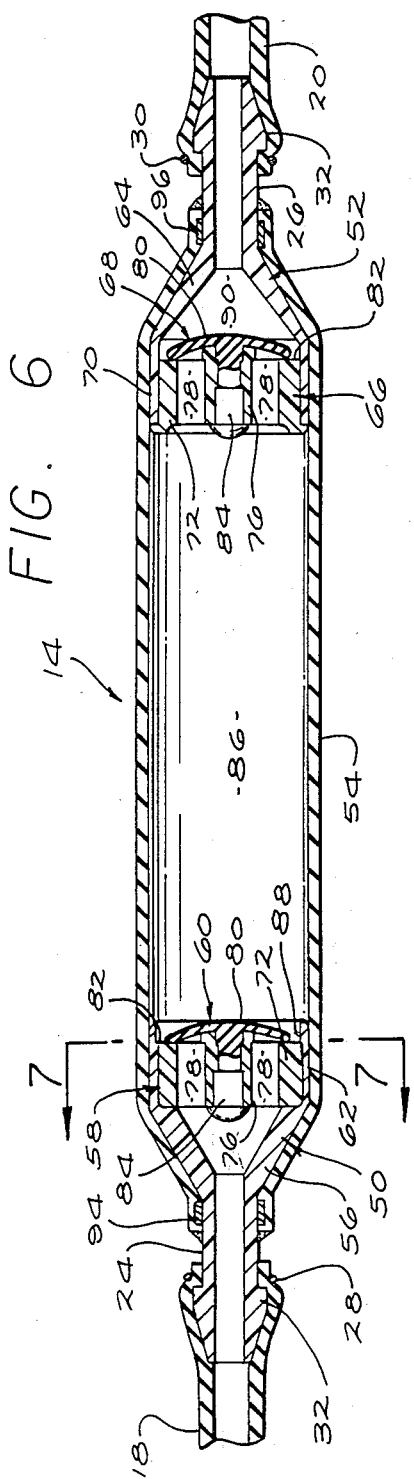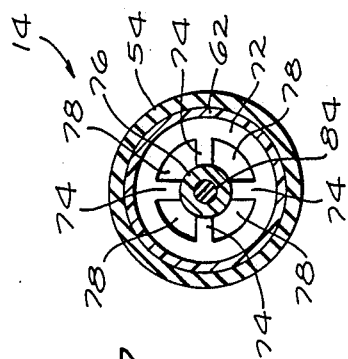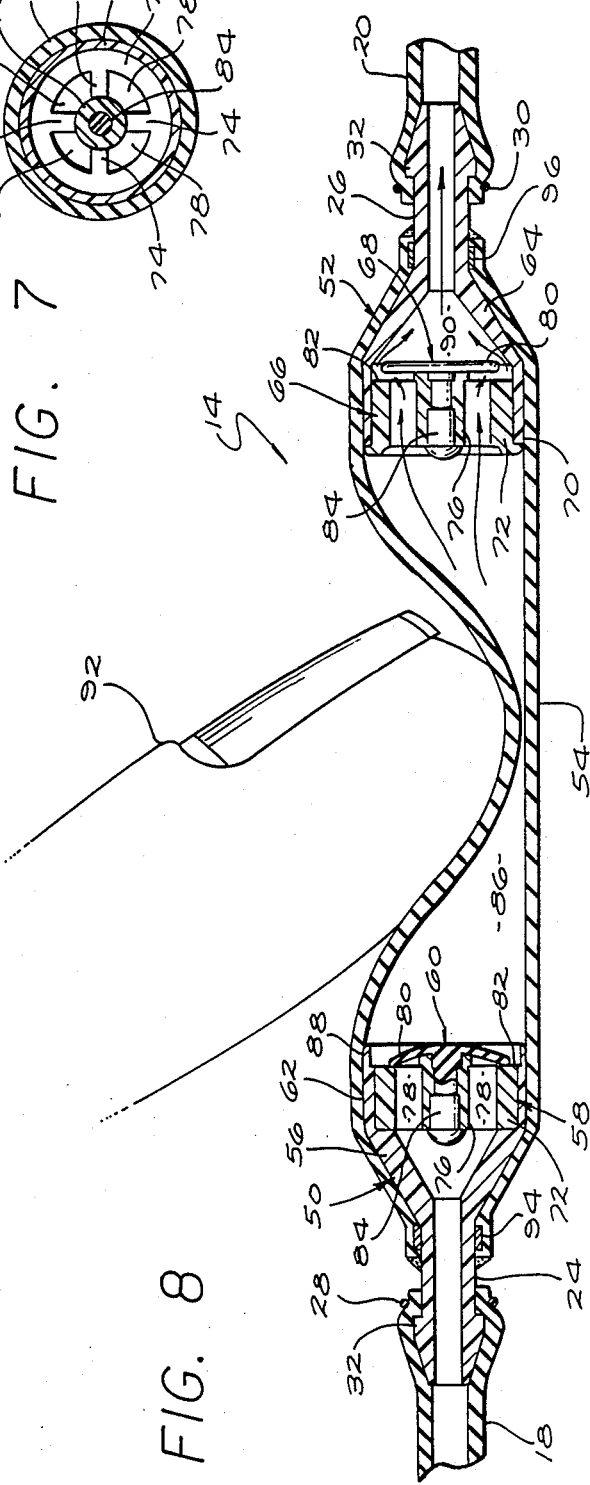

MULTIPLE-MEMBRANE FLOW CONTROL VALVE AND IMPLANTABLE SHUNT SYSTEM

BACKGROUND OF THE INVENTION

This invention relates generally to surgically implanted shunt systems and related flow control valves. More particularly, this invention relates to multiple-membrane one-way flow control valves for controlling the flow of cerebrospinal fluid out of a brain ventricle and preventing back flow of fluid into the brain ventricle.

As is well known in the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids which ought to drain away instead accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart.

Many such devices have been previously used, but several of these devices have tended to become obstructed by particulate matter entering the drainage system or by the backward diffusion of blood into the system. Further, some prior devices have included moving parts which tended to adhere to other parts of the device and become immobile. When this occurs, the device itself becomes a barrier in the drainage system, and adds to the problem it is intended to solve.

Moreover, manufacturers have been faced with a dilemma regarding the use of metal components in such valves. Some prior devices have included metal components which tended to interfere with X-ray photography and produce radiation scatter ("sunburst effect") on films taken by computerized axial tomography (CAT) scanning equipment, and such X-ray photography and CAT scanning frequently accompanies the use of surgically implanted flow control valves. However, it is desirable in some instances to be able to ascertain specific information from an implanted device by X-ray photography without having to reopen the patient's skin. For instance, it is sometimes desirable to provide an X-ray detectable marker which can facilitate detection of a separation of drainage tubing from the valve.

Accordingly, there has been a continuing need in the medical arts for convenient and effective devices for controlling the flow of fluid from one part of the human body to another, which devices are relatively inexpensive to manufacture and can be constructed substantially of nonmetallic parts which are not subject to adhering to one another and causing malfunction of the device. Further, such a device is needed which utilizes multiple valve membranes in series for safety and reliability. As will become apparent from the following description, the present invention satisfies these needs and provides other related advantages.

SUMMARY OF THE INVENTION

The present invention resides in a shunt system for controlling the flow of fluids from one part of the human body to another, which is constructed substantially of nonmetallic materials and provides trouble-free and reliable operation in use. The system of the present invention is relatively inexpensive to manufacture, and can be easily modified to provide a variety of pressure/flow characteristics. In accordance with the present invention, the shunt system includes antechamber means for injecting medication into the shunt system, and a multiple-membrane flow control valve for controlling the flow of fluid from one portion of the human body to another.

In the preferred embodiment, the flow control valve includes a pair of relatively rigid bases which are invested within a relatively flexible encasement. Each base includes an outer housing, a valve membrane carrier securely positioned within the outer housing, and an inlet/outlet connector integrally formed with the outer housing. The bases define inlet/outlet fluid passageways, and are positioned within the encasement such that the encasement defines an intermediate fluid passageway between the inlet/outlet fluid passageways. Further, the encasement is deformable by external pressure to facilitate manual flushing of the valve.

A relatively flexible flow control member, molded of a nonmetallic material different from the material of the bases, is mounted to each base. Each flow member includes a central support attached to the valve membrane carrier, and a resilient membrane which is generally arch-shaped and resiliently biased to normally contact the respective base generally along the outer edge of the membrane in a manner permitting only controlled uni-directional flow of fluid through the base. Such valve construction normally prevents flow of fluid through the valve, but permits the resilient membrane to open to permit fluid flow through the valve when the upstream fluid pressure exceeds the downstream fluid pressure by a predetermined amount.

Moreover, a variety of pressure/flow characteristics can be provided by the flow control valve of the present invention by providing such valves with different resilient membranes of varying thicknesses. The resistance to flow through the valves increases with an increase in membrane thickness.

In order to provide the desired resistance to adhesion between the base and the resilient membrane, particularly during storage of the valve, the base is preferably formed of polypropylene material and the membrane is preferably formed of a silicone elastomer material. Further, the flexible encasement which cooperates with the base to form an intermediate fluid passageway is also preferably molded of a silicone elastomer material.

The base adjacent to the inlet preferably includes a relatively rigid recess in which the membrane is positioned to protect it against deformation when the flexible encasement is manually manipulated. With a similar purpose, the base adjacent the outlet includes an outlet chamber in which the membrane is positioned. Further, the valve membrane carriers each define a plurality of channels which are collectively covered by the adjacent flow control members.

Radiopaque markers are located on the inlet/outlet connectors to allow verification of a valve to drain disconnect, by X-ray, if radiopaque surgical tubing separates from the valve after implantation of the system in the body.

The antechamber means includes, generally, a rigid needle guard situated within a relatively flexible encasement. The structure of the antechamber means, and its position relative to a proximal catheter and the distal flow control valve, permits the injection of medication into the shunt system, and provides means for pumping the medication either distally or proximally.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is an enlarged sectional view of the flow control valve, taken generally along the line 6—6 of FIG. 2;

FIG. 7 is an elevational sectional view taken generally along the line 7—7 of FIG. 6, illustrating the position of a valve membrane carrier within the outer housing of a base, and fluid flow channels through the membrane carrier; and FIG. 8 is a sectional view similar to FIG. 6, illustrating one method of flushing the valve in the distal direction.

DETAILED DESCRIPTION OF THE PREFERRED EMBODIMENT

Figure 1:
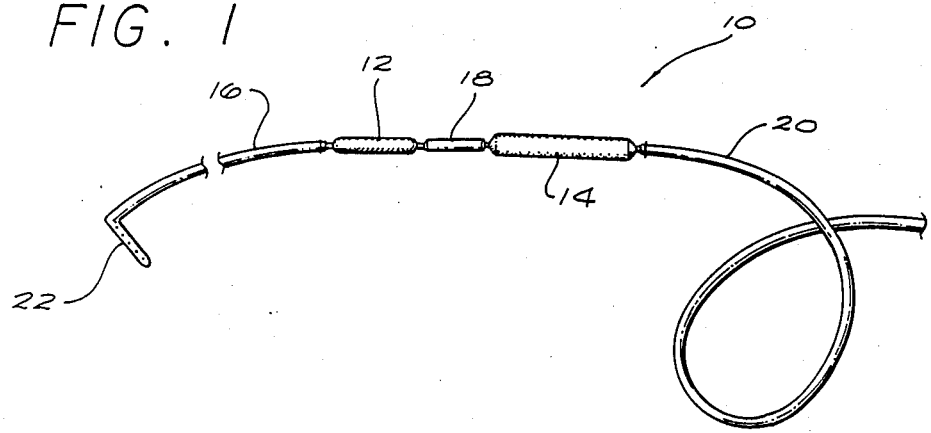
FIG. 1 is a perspective environmental view of the shunt system of the present invention, illustrating the relative positioning of an antechamber and a multiple-membrane flow control valve with respect to a proximal catheter and inter-connective surgical tubing.
Figure 2:
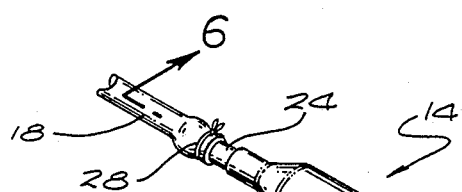
FIG. 2 is an enlarged perspective view of the flow control valve illustrated in FIG. 1.
Figure 3:
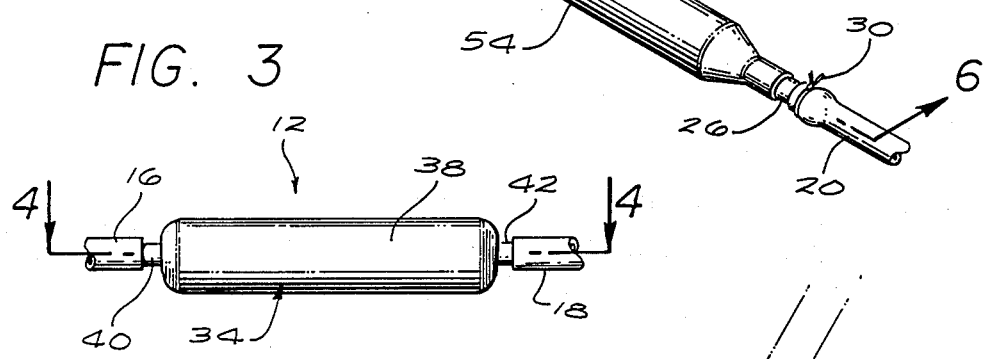
FIG. 3 is an enlarged perspective view of the antechamber illustrated in FIG. 1.

As shown in the drawings for purposes of illustration, the present invention is concerned with a surgically implantable shunt system, generally designated in FIG. 1 by the reference number 10. This improved shunt system 10 includes, broadly, an antechamber 12 and a multiple-membrane flow control valve 14, which are connected by segments of surgical tubing 16, 18 and 20 to drain fluids from one portion of the human body to another. When the system 10 is used in the treatment of hydrocephalus, the antechamber 12 and the flow control valve 14 form portions of a fluid conduit extending from a proximal catheter 22, which is inserted through the skull into a brain ventricle containing cerebrospinal fluid under pressure, to a distal catheter (not shown), which serves to discharge cerebrospinal fluid into, for example, the atrium portion of a patient's heart.

In order to connect the valve 14 to segments of the surgical tubing 18 and 20, the valve is provided an inlet connector 24 and an outlet connector 26 which each receive one end of the sections of surgical tubing 18 and 20, respectively. The ends of the tubing 18 and 20 slide over the connectors 24 and 26, and each is secured to its respective connector by a single ligature 28 and 30. The ligatures are preferably secured around the tubing just inside an annular ridge 32 formed near the end of each connector (FIGS. 6 and 8).

As will become apparent below, the shunt system of the present invention provides a highly reliable valve designed to prevent valve seat deformation and membrane to valve seat sticking. The shunt system of the present invention is inexpensive to produce and is designed to facilitate implantation by minimizing components to be connected or adjusted other than the surgical tubing of the shunt system. The use of metal as a functional component has also been eliminated. Moreover, positioning concerns relating to the valve have been minimized through the provision of a cylindrical design. Thus, due to the symmetry of the system, there is no top or bottom which must be anchored in place over the patient's skull for proper operation.

In accordance with the present invention, and as illustrated in FIGS. 1 and 3 through 5, the antechamber 12 includes a flexible, generally cylindrical housing 34 and a relatively rigid needle shield 36 positioned within the housing 34. The housing 34 includes an enlarged central section 38 in which the needle shield 36 is positioned, an inlet connector 40 at one end of the central section, and an outlet connector 42 at the other. The inlet and outlet connectors 40 and 42 are dimensioned to be received, respectively, within adjoining ends of the segments of surgical tubing 16 and 18, and are secured therein by a suitable adhesive. When connected as shown, fluid flowing through the shunt system 10 from the proximal catheter 22 to the valve 14, must first pass through the antechamber 12.

Figure 5:
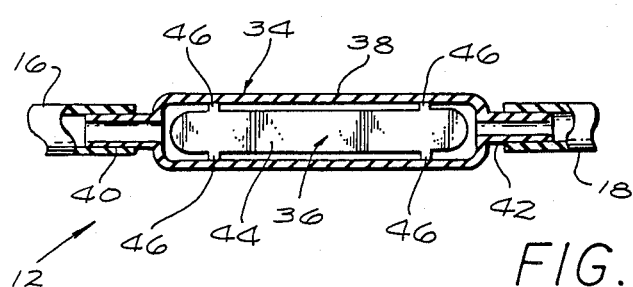
FIG. 5 is a sectional view of the antechamber taken generally along the line 5—5 of FIG. 4.

The needle shield 36 is preferably constructed of a polypropylene material to form a plate 44 within the central section 38 of the housing 34. A polypropylene material is preferred for the needle shield 36 in order to minimize any potential sticking between the housing 34, which is preferably constructed of a silicone elastomer material, and the needle shield. As illustrated in FIG. 5, the needle shield 36 includes four attachment stubs 46 which are fixed to the inner surface of the central section 38 of the housing 34. This tends to rigidly fix the plate 44 centrally within the housing 34.

Figure 4:
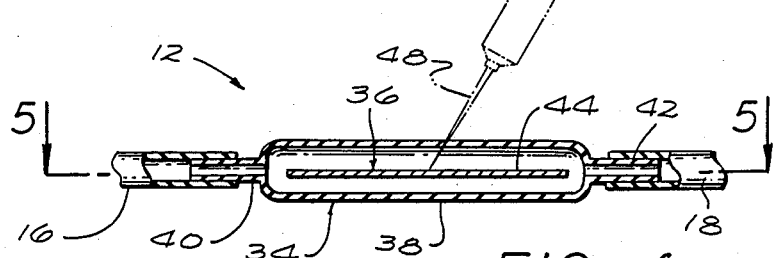
FIG. 4 is a sectional view of the antechamber taken generally along the line 4—4 of FIG. 3, which illustrates, among other things, the manner in which a needle shield is utilized for the injection of medication into the antechamber.

As illustrated in FIG. 4, the housing 34 of the antechamber 12 can be punctured by a needle 48 in order to inject medication into the shunt system 10. The silicone elastomer material of the housing 34 has a sufficient thickness to permit insertion of a twenty-five gauge or smaller needle 60 without affecting the ability of the housing to reseal after the needle has been withdrawn. The polypropylene material of the needle shield 36 has sufficient rigidity to prevent the needle 60 inserted through the housing 34 from passing all the way through the antechamber 12. This permits the physician to feel where the tip of the needle 60 is positioned during injection, to insure that the medication is being injected into the shunt system 10 and not into the surrounding tissue. Following the injection of medication, the antechamber 12 can then be used as a pump for directing the medication toward the proximal catheter 22 or toward the flow control valve 14.

To pump medication within the antechamber 12 toward the proximal catheter 22, the physician simply depresses the section of surgical tubing 18 between the antechamber 12 and the valve 14 through manual percutaneous pressure, and then depresses the housing 34 of the antechamber to flush the contents thereof through the proximal section of the surgical tubing 16. In a similar manner, the medication within the antechamber can be pumped distally toward the valve 14. This is accomplished by percutaneously occluding the proximal surgical tubing 16, and then depressing the housing 34 to flush medication therein through the intermediate section of surgical tubing 18 to the valve 14.

With reference now to FIGS. 1, 2 and 6 through 8, the flow control valve 14 includes a first base 50 positioned adjacent an inlet of the valve, and a second base 52 positioned adjacent an outlet of the valve. These bases 50 and 52 are invested within a flexible encasement 54.

The first base 50 includes a first outer housing 56, a first valve membrane carrier 58 securely positioned within the first outer housing, and the inlet connector 24 which is integrally formed with the first outer housing 56. The first valve membrane carrier provides a cylindrical support for a first flow control member 60, and is press-fit within a support portion 62 provided by the first outer housing 56.

Similarly, the second base 52 includes a second outer housing 64, a second valve membrane carrier 66 securely positioned within the second outer housing, and the outlet connector 26 which is integrally formed with the second outer housing 64. The second valve membrane carrier provides a cylindrical support for a second flow control member 68, and is press-fit within a support portion 70 provided by the second outer housing 64.

Each of the valve membrane carriers 58 and 66 include a cylindrical outer portion 72 which abuts against a correspondingly shaped inner surface of the support portions 62 and 70 to form a fluid tight seal therebetween. Supporting vanes 74 extend radially inwardly from this cylindrical outer portion 72 to form a central mount 76 for the flow control members 60 and 68. The vanes 74 form a plurality of channels 78 through which fluid is permitted to flow.

The flow control members 60 and 68 are arranged serially within the valve 14 for controlling the flow of cerebrospinal fluid out of a brain ventricle and preventing backflow of fluid into the brain ventricle by the provision of resilient nonmetallic membranes 80. The membranes 80 are molded of a synthetic polymer material different from the material of the valve membrane carriers 58 and 66, and are secured to the valve membrane carriers in a manner covering the channels 78 therethrough. The resilient membranes 80 are normally biased to close communication between the inlet connector 24 and the outlet connector 26, but will open to permit flow when the pressure on the proximal side of a resilient membrane 80 exceeds the pressure on the distal side by a predetermined amount. Moreover, should the pressure on the distal side of the resilient membranes 80 ever exceed the pressure on the proximal side, tending to cause flow in a reverse direction through the valve 14, the membranes 80 will seal tightly against the respective valve membrane carrier 58 and 66, sealing the channels 78 and preventing any such reverse flow.

More specifically, the outer housings 56 and 64, and the valve membrane carriers 58 and 66 are preferably formed of a polypropylene material, and the membranes 80 are preferably formed of an elastomer material, preferably a silicone elastomer material. Both polypropylene and elastomer materials have been shown to produce an acceptable level of tissue reaction, and the use of this particular duality of materials, in contrast to the use of only a single material, markedly decreases the chance of the membranes 80 adhering to any portion of the bases 50 and 52, which would clog the drain passage and defeat the purpose of the valve 14.

An added advantage of using these particular materials is the avoidance of the negative effect of metal components, due to radiation scatter or "sunburst effect," on films taken by, for example, computerized axial tomography (CAT) scanning equipment. This type of scanning frequently accompanies the use of surgically implanted flow control valves, and the absence or limitation of metal in the area scanned will permit more accurate and complete results to be gathered from CAT scanning.

The membranes 80 have an arch-shape, as for example a section of a sphere, and each contacts the distal edge 82 of the respective valve membrane carrier 58 and 66 generally along the outer edges of the membrane in a manner surrounding the channels 78. Each membrane 80 is secured to the respective valve membrane carrier 58 and 66 by a central support 84 which is received in the central mount 76 and fixed thereto by an interference fit or by use of an adhesive, or any other suitable means.

Since the valve 14 of the present invention is primarily designed to provide controlled resistance to cerebrospinal fluid flow from a brain ventricle to another location in the body, such as the atrium portion of the patient's heart, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated. Toward this end, in order to provide a variety of valves having different pressure/flow characteristics, the valve 14 can be provided with thick membranes or relatively thin membranes. Resistance to flow increases with the increase in membrane thickness.

As illustrated best in FIGS. 6 and 8, the first and second bases 50 and 52 are separated from one another within the flexible encasement 54, so that the central section of the encasement can be deformed by external pressure to facilitate manual flushing of the valve 14. This central portion of the encasement 54 defines an intermediate fluid passageway 86 between an inlet fluid passageway provided through the first base 50, and an outlet fluid passageway provided through the second base 52.

In order to protect the resilient membranes 80 against possible deformation which may occur through the percutaneous manipulation of the valve 14, the first base 50 is provided a membrane shield 88 integrally formed with the first outer housing 56, which extends outwardly from the valve seat or distal edge 82 of the first valve member carrier 58. This membrane shield 88 effectively forms a recess in which the first flow control member 6 is situated. The second flow control member 68 is similarly protected against deformation due to percutaneous pressure, by situating the resilient membrane 80 thereof within an outlet chamber 90 provided between the second valve membrane carrier 66 and the outlet connector 26. The second flow control member 68 is thus completely surrounded by portions of the rigid second base 52 to completely protect it against deformation due to percutaneous manipulation of the flow control valve 14.

To flush the flow control valve 14, the intermediate portion of the flexible encasement 54 is pressed downwardly (as shown by a finger 92 in FIG. 8) to force fluid within the intermediate fluid passageway 86 through the channels 78 of the second valve membrane carrier 66, and past the second flow control member 68 to the outlet connector 26. Upon withdrawal of the percutaneous pressure from the flexible encasement 54, the second flow control member 68 will again engage the distal edge 82 of the second valve membrane carrier 66 to prevent the reverse flow of fluid through the channels 78.

Radiopaque barium sulfate-impregnated markers 94 and 96 are provided which wrap around a portion of the connectors 24 and 26. The radiopaque markers 92 and 94 provide means whereby a physician can detect a separation of the surgical tubing 18 and 20 from the valve 14 after implantation. Such valve/tubing disconnect is readily detectable in the shunt system 10 through the use of X-ray photography when radiopaque surgical tubing is connected to the valve 14.

From the foregoing it will be appreciated that the shunt system of the present invention provides a device by which the flow of cerebrospinal fluid out of a brain ventricle can be controlled while preventing the backflow of fluid into the brain ventricle, and by which the chance of a valve clogging the drain passage can be greatly decreased. The antechamber 12 and the valve 14 can be fabricated conveniently and economically, are trouble-free and reliable in use, provide convenient flushing of the shunt system, and can be easily adapted to provide a variety of pressure/flow characteristics. Further, the inclusion of radiopaque indicators provides the surgeon means for ascertaining specific information about the device which would otherwise be unavailable without additional surgery. Moreover, through the provision of multiple flow control members within the valve 14, the possibility of a misfunction within the valve itself is minimized, thereby assuring the physician and the patient that the desired resistance to fluid flow through the shunt system will be maintained at all times.

Although a particular embodiment of the invention has been described in detail for purposes of illustration, various modifications may be made without departing from the spirit and scope of the invention. Accordingly, the invention is not to be limited, except as by the appended claims.

We claim:

1. A surgically implantable shunt system, comprising:
    antechamber means for injecting medication into the shunt system; and
    a flow control valve for controlling the flow of fluid from one portion of the human body to another, the valve including:
    an inlet in closed communication with the antechamber means, the inlet including an inlet connector,
    an outlet including an outlet connector,
    a first base adjacent to the inlet, the first base including an inlet fluid passageway therethrough and a first valve seat surrounding a portion of the inlet fluid passageway, wherein at least a portion of the first base is integrally formed with the inlet connector,
    a first flow control member including a central support and a resilient first membrane, the central support being attached to the first base and extending therefrom to support the first membrane, the first membrane being arch-shaped so that the outer edges of the first membrane contact the first valve seat,
    a second base adjacent to the outlet, the second base including an outlet fluid passageway therethrough and a second valve seat surrounding a portion of the outlet fluid passageway, wherein at least a portion of the second base is integrally formed with the outlet connector, the outlet connector and the portion of the second base integrally formed therewith cooperatively defining a relatively rigid protective outlet chamber.
    a second flow control member including a central support and a resilient second membrane, the central support being attached to the second base and extending therefrom to support the second membrane within the outlet chamber, the second membrane being generally arch-shaped so that the outer edges of the second membrane contact the second valve seat, and
    a flexible encasement generally surrounding the first and second bases, wherein the encasement is deformable by external pressure to facilitate manual flushing of the valve, and defines an intermediate fluid passageway between the inlet and the outlet fluid passageways.

2. A shunt system as set forth in claim 1, wherein the first base includes an outer housing within which a separate valve membrane carrier is press-fit, the valve membrane carrier including a support structure for positioning the central support of the first flow control member so that the first membrane is supported within a relatively rigid protective recess provided by the outer housing.

3. A shunt system as set forth in claim 2, wherein the valve membrane carrier defines a plurality of channels comprising at least part of the inlet fluid passageway, wherein the channels are collectively occluded in a controlled manner by the first flow control member.

4. A shunt system as set forth in claim 1, wherein the second base includes an outer housing within which a separate valve membrane carrier is press-fit, the valve membrane carrier including a support structure for positioning the central support of the second flow control member so that the second membrane is supported within the outlet chamber and contacts the second valve seat to occlude the same in a controlled manner.

5. A shunt system as set forth in claim 4, wherein the valve membrane carrier defines a plurality of channels, and wherein the second valve seat is situated on the valve membrane carrier.

6. A shunt system as set forth in claim 1, wherein the antechamber means includes a rigid needle guard situated within a relatively flexible encasement.

7. An implantable flow control valve for controlling the flow of fluid from one portion of the human body to another, said valve comprising:
    an inlet;
    an outlet;
    a first base adjacent to the inlet, the first base including an inlet fluid passageway therethrough and a first valve seat surrounding a portion of the inlet fluid passageway;
    a first flow control member including a central support and a resilient first membrane, the central support being attached to the first base and extending therefrom to support the first membrane, the first membrane being generally arch-shaped and contacting the first valve seat in a manner to occlude the inlet fluid passageway;

a second base adjacent to the outlet, the second base including an outlet fluid passageway therethrough and a second valve seat surrounding a portion of the outlet fluid passageway;

a second flow control member including a central support and a resilient second membrane, the central support being attached to the second base and extending therefrom to support the second membrane, the second membrane being generally arch-shaped and contacting the second valve seat in a manner occluding the outlet fluid passageway; and a flexible encasement generally surrounding the first and second bases, wherein the encasement is deformable by external pressure to facilitate manual flushing of the valve, and defines an intermediate fluid passageway between the inlet and the outlet;

wherein the first base includes a first outer housing within which a separate first valve membrane carrier is press-fit, the first valve membrane carrier including a support structure for positioning the central support of the first flow control member so that the outer edges of the first membrane contact the first valve seat; and wherein the second base includes a second outer housing within which a separate second valve membrane carrier is press-fit, the second valve membrane carrier including a support structure for positioning the central support of the second flow control member so that the outer edges of the second membrane contact the second valve seat.

8. A valve as set forth in claim 7, wherein the inlet includes an inlet connector integrally formed with at least a portion of the first base.

9. A valve as set forth in claim 8, wherein the outlet includes an outlet connector integrally formed with at least a portion of the second base.

10. A valve as set forth in claim 9, wherein the second base and the outlet connector cooperatively define an outlet chamber between the second base and the outlet, and wherein the second membrane is positioned within the outlet chamber.

11. A valve as set forth in claim 7, wherein the first base includes a relatively rigid recess in which the first membrane is positioned.

12. A valve as set forth in claim 7, wherein the second valve membrane carrier defines a plurality of channels comprising a part of the outlet fluid passageway, and wherein the second valve seat is situated on the second valve membrane carrier.

13. A valve as set forth in claim 7, including an inlet radiopaque marker generally encircling a portion of the inlet.

14. A valve as set forth in claim 7, including an outlet radiopaque marker generally encircling a portion of the outlet.

15. A surgically implantable flow control valve for controlling the flow of fluid from one portion of the human body to another, said valve comprising:

a first base including a first outer housing within which a first valve membrane carrier is press-fit, and an inlet connector integral with the first outer housing, the first base defining an inlet fluid passageway;

a second base including a second outer housing within which a second valve membrane carrier is press-fit, and an outlet connector integral with the second outer housing, the second base defining an outlet fluid passageway;

a flexible encasement generally surrounding the first and second bases, wherein the encasement is deformable by external pressure to facilitate manual flushing of the valve, the flexible encasement defining an intermediate fluid passageway between the inlet and the outlet fluid passageways;

a first flow control member including a central support and a resilient first membrane, the central support being attached to the first valve membrane carrier and the first membrane being generally arch-shaped and resiliently biased to normally contact the first base in a manner permitting only controlled uni-directional flow through the inlet fluid passageway; and a second flow control member including a central support and a resilient second membrane, the central support being attached to the second valve membrane carrier, and the second membrane being generally arch-shaped and resiliently biased to normally contact the second base in a manner permitting only controlled uni-directional flow through the outlet fluid passageway;

wherein the second outer housing and the outlet connector cooperatively define an outlet chamber adjacent to the second valve membrane carrier, wherein the second membrane is positioned within the outlet chamber.

16. A valve as set forth in claim 15, wherein the first base includes a relatively rigid recess in which the first membrane is positioned.

17. A valve as set forth in claim 15, wherein the first and second valve membrane carriers define a plurality of channels which are collectively covered, and thereby fluid flow is effectively controlled therethrough by, respectively, the first and second flow control members.

18. A valve as set forth in claim 15, including antechamber means for injecting medication into a shunt system, wherein the antechamber means is placed in fluid communication with the valve inlet fluid passageway.

* * * * *